United States Patent
Sotiriou

(10) Patent No.: US 8,257,242 B2
(45) Date of Patent: *Sep. 4, 2012

(54) MAGNETIC THERAPY DEVICE

(76) Inventor: George Sotiriou, Farmingville, NY (US)

(*) Notice: Subject to any disclaimer, the term of this patent is extended or adjusted under 35 U.S.C. 154(b) by 1215 days.

This patent is subject to a terminal disclaimer.

(21) Appl. No.: 11/875,477

(22) Filed: Oct. 19, 2007

(65) Prior Publication Data

US 2009/0105520 A1 Apr. 23, 2009

(51) Int. Cl.
*A61B 17/52* (2006.01)
(52) U.S. Cl. .......................................... 600/9
(58) Field of Classification Search ............ 600/9–15
See application file for complete search history.

(56) References Cited

U.S. PATENT DOCUMENTS

| | | | |
|---|---|---|---|
| 4,228,387 A | 10/1980 | Brown | |
| 4,340,890 A | 7/1982 | Fritze | |
| 4,350,937 A | 9/1982 | Miyazaki et al. | |
| 4,537,181 A | 8/1985 | Shalhoob | |
| 4,727,857 A | 3/1988 | Horl | |
| 5,632,720 A | 5/1997 | Kleitz | |
| 5,667,469 A | 9/1997 | Zhang | |
| 5,762,599 A | 6/1998 | Sohn | |
| 6,001,055 A | 12/1999 | Souder | |
| 6,065,210 A | 5/2000 | Bove | |
| 6,092,531 A * | 7/2000 | Chen et al. | 128/899 |
| 6,123,657 A | 9/2000 | Ishikawa | |
| 6,155,966 A | 12/2000 | Parker | |
| 6,231,497 B1 | 5/2001 | Souder | |
| 6,238,333 B1 | 5/2001 | Loos | |
| 6,245,006 B1 | 6/2001 | Olson | |
| 6,265,984 B1 | 7/2001 | Molinaroli | |
| 6,461,377 B1 | 10/2002 | An | |
| 6,626,818 B2 | 9/2003 | Sexton | |
| 6,648,812 B2 | 11/2003 | Ardizzone | |
| 6,663,557 B2 | 12/2003 | Werny | |
| 6,679,825 B2 | 1/2004 | Alicea | |
| 6,781,697 B1 | 8/2004 | Carra et al. | |
| 7,803,104 B2 * | 9/2010 | Sotiriou | 600/9 |
| 7,915,846 B2 * | 3/2011 | Sotiriou | 318/445 |
| 2002/0147380 A1 * | 10/2002 | Ardizzone | 600/9 |
| 2004/0122281 A1 | 6/2004 | Fischell et al. | |
| 2004/0150372 A1 | 8/2004 | Lee et al. | |
| 2005/0034902 A1 * | 2/2005 | Madhavarao et al. | 177/136 |
| 2007/0083074 A1 | 4/2007 | Sotiriou | |
| 2009/0102587 A1 | 4/2009 | Sotiriou | |
| 2009/0103332 A1 | 4/2009 | Sotiriou | |
| 2009/0105519 A1 | 4/2009 | Sotiriou | |
| 2010/0081858 A1 | 4/2010 | Sotiriou | |

OTHER PUBLICATIONS

Office Action received for U.S. Appl. No. 11/875,465, mailed on Aug. 5, 2009, 14 pages. Office Action received for U.S. Appl. No. 11/875,465, mailed on Feb. 5, 2010, 17 pages.
U.S. Appl. No. 11/875,452, filed Oct. 19, 2007.
U.S. Appl. No. 11/875,459, filed Oct. 19, 2007.
U.S. Appl. No. 11/875,465, filed Oct. 19, 2007.

* cited by examiner

*Primary Examiner* — Christine Matthews
(74) *Attorney, Agent, or Firm* — Brake Hughes Bellermann LLP; Shane A. Kennedy

(57) ABSTRACT

Various example embodiments are disclosed. According to one example embodiment, a magnetic therapy device may include a power source, a motor, a tachometer, and a microprocessor. The power source may be configured to supply power to the motor. The motor may be configured to control a disk upon which is mounted a plurality of magnets. The tachometer may be configured to monitor a magnetic field generated by the plurality of magnets and provide a signal to a microprocessor based on the monitored magnetic field. The microprocessor may be configured to control the motor based on the signal received from the tachometer.

20 Claims, 6 Drawing Sheets

US 8,257,242 B2

MAGNETIC THERAPY DEVICE

TECHNICAL FIELD

This description relates to electrical circuits.

BACKGROUND

Magnetic therapy has been found to have therapeutic effect on humans. Subjecting parts of the human body to magnetic fields may have beneficial effects.

SUMMARY

According to one general aspect, a magnetic therapy device may include a power source, a motor, a tachometer, and a microprocessor. The power source may be configured to supply power to the motor. The motor may be configured to control a disk upon which is mounted a plurality of magnets. The tachometer may be configured to monitor a magnetic field generated by the plurality of magnets and provide a signal to a microprocessor based on the monitored magnetic field. The microprocessor may be configured to control the motor based on the signal received from the tachometer.

The details of one or more implementations are set forth in the accompanying drawings and the description below. Other features will be apparent from the description and drawings, and from the claims.

DETAILED DESCRIPTION

Figure 1:
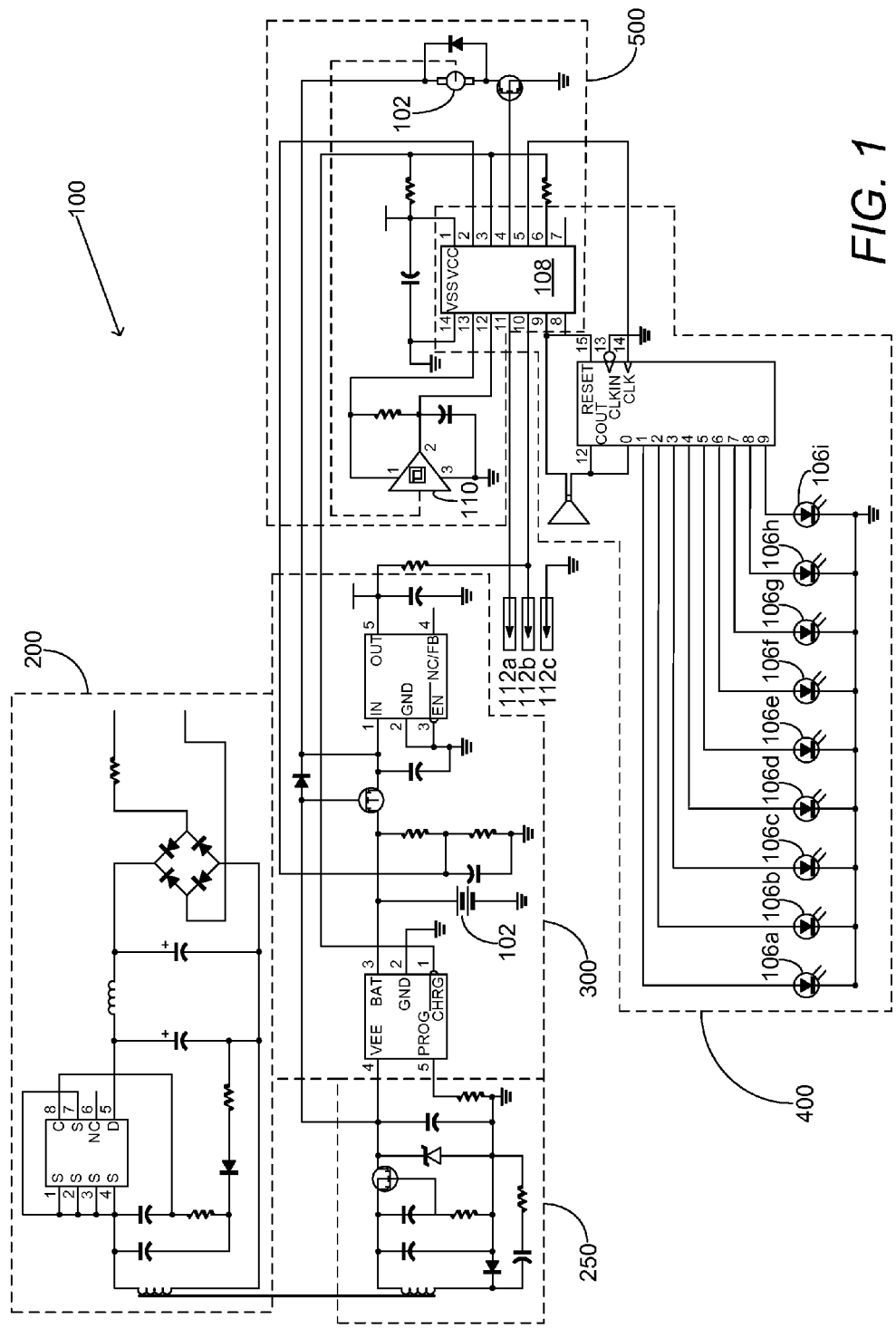
FIG. 1 is a circuit diagram showing a system according to an example embodiment.

FIG. 1 is a circuit diagram showing a system 100 according to an example embodiment. According to this example, the system 100 may include a charging probe circuit 200. The charging probe circuit 200 may, for example, receive current from an alternating current source an induce a magnetic field. The charging probe circuit 200 is described further with reference to FIG. 2.

The system 100 may also include a current inducing circuit 250. The current inducing circuit 250 may carry a current induced by a magnetic field such as the magnetic field induced by the charging probe circuit 200. The current inducing circuit 250 may produce an electrical output based on the magnetic field. The current inducing circuit 250 is described in further detail with reference to FIG. 2.

The system 100 may also include a battery charging circuit 300. The battery charging circuit 300 may receive a voltage source, such as the electrical output of the current inducing circuit, and recharge a rechargeable battery 102 with the voltage source. The battery charging circuit 300 may supply power to a motor 104. The battery charging circuit 300 may, for example, allow current to flow from the voltage source to the motor 104. The battery charging circuit 300 may also enable the rechargeable battery 102 to supply power to the motor 104 when a voltage of the voltage source drops below a threshold voltage level, according to an example embodiment. The battery charging circuit 300 is described in further detail with reference to FIG. 3.

The system 100 may also include a visual indicating circuit 400. The visual indicating circuit 400 may, for example, include a plurality of visual indicators 106a, 106b, 106c, 106d, 106e, 106f, 106g, 106h, 106i and a microprocessor 108 which monitors a voltage level of a rechargeable battery, such as the rechargeable battery 102 included in the battery charging circuit 300. The visual indicating circuit 400 may light a number of the plurality of visual indicators 106a, 106b, 106c, 106d, 106e, 106f, 106g, 106h, 106i based on a monitored voltage level of the rechargeable battery 102, according to an example embodiment. The visual indicating circuit 400 is described in further detail with reference to FIG. 4.

The system 100 may also include a tachometer circuit 500. The tachometer circuit 500 may include a motor 104 which controls a disk (shown in FIG. 6D) upon which is mounted a plurality of magnets (also shown in FIG. 6D). The tachometer circuit 500 may also include a tachometer 110 which monitors a magnetic field generated by the plurality of magnets and provides a signal to a microprocessor based on the monitored magnetic field. The tachometer circuit 500 may also include a microprocessor, which may be the same microprocessor 108 used by the visual indicating circuit 400, which controls the motor 104 based on the signal received from the tachometer 110. The tachometer circuit 500 is described further with reference to FIG. 5.

The system 100 may include one or more microprocessor inputs 112a, 112b, and may include an input ground 112c. The microprocessor inputs 112a, 112b may be used to program the microprocessor 108, such as by use of a personal computer (not shown), according to an example embodiment.

Figure 2:
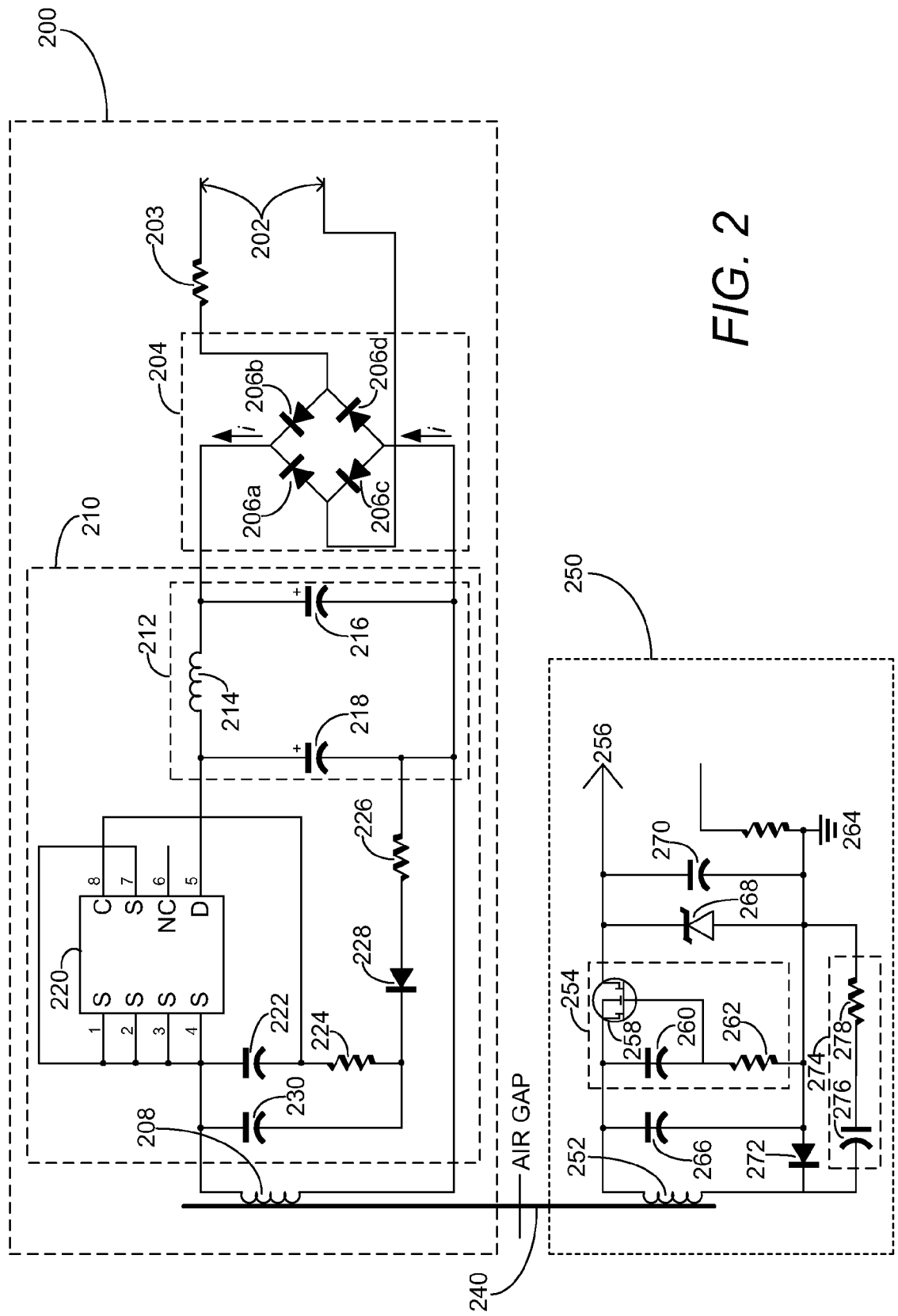
FIG. 2 is a circuit diagram showing a charging probe circuit and current inducing circuit according to an example embodiment.

FIG. 2 is a circuit diagram showing the charging probe circuit 200 and current inducing circuit 250 according to an example embodiment. According to this example, the charging probe circuit 200 may include an alternating current (AC) input 202. The AC input 202 may receive current from an AC source (not shown), such as an electrical wall outlet (not shown). The AC input 202 may, for example, receive inputs between approximately 85 to 264 volts AC between approximately 47 and 64 Hertz. This may allow the charging probe circuit 200 to receive input from many electrical wall outlets.

The AC input 202 may be coupled to a rectifier circuit 204. The rectifier circuit 204 may rectify the current received by the AC input 202 from the AC source. The rectifier circuit 204 may include a bridge rectifier circuit. The rectifier circuit 204 may, for example, include a plurality, such as four, diodes 206a, 206b, 206c, 206d which allow current to flow through the rectifier circuit 204 in only one direction, such as the direction denoted i in FIG. 2.

One of the AC input 202 nodes may be coupled to the rectifier circuit 204 via a resistor 203. The resistor 203 may, for example, include a flameproof fusible resistor. The resistor 203 may protect against fault conditions. In an example embodiment, The charging probe circuit may also include a primary coil 208 and a control circuit 210. The control circuit 210 may convert the rectified current into a regulated voltage across the primary coil 208. The primary coil 208 may induce a magnetic field from the regulated voltage. The magnetic field may, for example, have a frequency between about ten Hertz and about one hundred Hertz.

The primary coil 208 may include a first end coupled to the control circuit 210 and a second end coupled to the rectifier circuit 204. The primary coil 208 may, in an example embodiment, extend away from the AC input 202, rectifier circuit 204, and control circuit 210. The primary coil 208 may be enclosed in a probe, as described further with reference to FIG. 6B.

In an example embodiment, the control circuit 210 may include a Pi filter 212. The Pi filter 212 may reduce ripple voltage across the rectifier circuit 204. The Pi filter 212 may, for example, include an inductor 214, a first capacitor 216, and a second capacitor 218. The input capacitance may be split between the first capacitor 216 and the second capacitor 218 to allow the Pi filter 212 to be formed by the inductor 214. The Pi filter 212. The Pi filter 212 may, for example, filter noise associated with the AC source.

The first capacitor 216 and second capacitor 218 may have capacitance values of, for example, approximately 4.7 microfarads and approximately 400 volts. The inductor 214 may, for example, have an inductance of approximately one milliHenry. The first capacitor 216 may have a first end coupled to a first end of the rectifier circuit 204 and to a first end of the inductor 214, and a second end coupled to a second end of the rectifier circuit 204 and to a first end of the primary coil 208. The first end of the inductor 214 may be coupled to the first end of the first capacitor 216 and to the first end of the rectifier circuit 204; a second end of the inductor 214 may be coupled to a first end of the second capacitor 218. A first end of the second capacitor 218 may be coupled to the second end of the inductor 214, and a second end of the second capacitor 218 may be coupled to the second end of the rectifier circuit 204 and the first end of the primary coil 208.

The control circuit 210 may also include an off-line regulator 220. The off-line regulator 220 may, for example, include a Power Integrations LK500, an integrated circuit which combines a 700 volt high voltage metal-oxide-semiconductor field-effect transistor (MOSFET), pulse-width modulation controller, startup, thermal shutdown, and fault protection circuitry.

The off-line regulator 220 may regulate the voltage across the primary coil 208. The off-line regulator 220 may, for example, be coupled to the primary coil 208. In an example embodiment, the off-line regulator 220 may be coupled to the second end of the inductor 214, and the rectifier circuit 204 may be coupled to the first end of the inductor 214.

In an example embodiment, the control circuit 210 may include a third capacitor 222 coupled to the primary coil 208. In this example, the off-line regulator 220 may regulate the voltage across the primary coil 208 by controlling a voltage across the third capacitor 222. The off-line regulator 220 may control the voltage across the third capacitor 222 by controlling a current flowing into or out of the off-line regulator 220 based on the voltage across the third capacitor 222. The third capacitor 222 may, for example, have a capacitance of 0.22 microfarads and approximately 50 volts.

For example, when power is applied, a high DC voltage may appear at a drain D of the off-line regulator 220. The third capacitor 222 may be charged through a switched high voltage current source connected internally between the drain D and a control C of the of the off-line regulator 220. When a voltage at the control C reaches approximately 5.7 volts relative to a source S of the off-line regulator 220, the internal current source of the off-line regulator 220 may be turned off. The internal control circuitry of the off-line regulator 220 may be activated and the high voltage internal MOSFET of the off-line regulator 220 may start to switch, using the energy stored in the third capacitor 222 to power the off-line regulator 220. As current ramps up in the primary coil 208, energy may be stored in the primary coil 208. The energy stored in the primary coil 208 may be delivered to the current inducing circuit 250 each cycle when the MOSFET turns off.

In another example, the off-line regulator 220 may include a source S coupled to a first end of the primary coil 208 and the drain D coupled to a first end of the second capacitor 218. In this example, the first end of the second capacitor 218 may be coupled to the drain D of the off-line regulator 220 and the second end coupled to the second end of the primary coil 208.

In an example embodiment, the drain D of the off-line regulator 220 may also be coupled to the second end of the inductor 214. A control C of the off-line regulator 220 may be coupled to a first end of the third capacitor 222. The source S of the off-line regulator 220 may also be coupled to a second end of the third capacitor 222 and to the first end of the primary coil 208.

In another example, the control circuit 210 may also include a first resistor 224, a second resistor 226, a diode 228, and a fourth capacitor 230. The diode 228 and fourth capacitor 230 may form a clamp network maintaining a voltage $V_{OR}$ at the first end of the primary coil 208. The diode 228 may include a fast ($t_{rr}$<250 nanoseconds) or ultra-fast diode to prevent the voltage across the off-line regulator 220 from reversing and ringing below ground. The second resistor 226 may filter leakage inductance.

The first resistor 224 may, for example, have a resistance of about 59.3 kiloohms. The fourth capacitor 230 may, for example, have a capacitance of one microfarad and 100 volts.

In an example embodiment, the fourth capacitor 230 may include a first end coupled to the source S of the off-line regulator 220 and to the first end of the primary coil 208. The fourth capacitor 230 may also include a second end coupled to a first end of the first resistor 224 and to a cathode end of the diode 228. The first resistor 224 may include a first end coupled to the second end of the fourth capacitor 230 and to the cathode end of the diode 228. A second end of the first resistor 224 may also include a second end coupled to the first end of the third capacitor 222 and to the control C. The diode 228 may include the cathode end coupled to the first end of the first resistor 224 and to the second end of the fourth capacitor 230, and an anode end coupled to a first end of the second resistor 226. The second resistor 226 may include the first end coupled to the anode end of the diode 228, and a second end coupled to the second end of the second capacitor 218, the second end of the first capacitor 216, the bridge circuit 204, and the second end of the primary coil 208.

The off-line regulator 220 may, for example, include three operating modes. In a startup mode, an output voltage across the fourth capacitor 230 may increase, and a current through the first resistor 224 and into the control C may increase from approximately zero to two milliamperes. In a regulate mode, the off-line regulator 220 may maintain a constant voltage across the third capacitor 222 by turning current into the control C off when the voltage across the third capacitor 222 increases, and turn the current into the control C on when the voltage across the third capacitor 222 decreases. In an auto-restart mode, which may be triggered by the voltage across the third capacitor falling so that the current into the control C falls below approximately one milliampere, the off-line regulator 220 may return to the startup mode. The third capacitor 222 may set the auto-restart period and the time for reaching the regulate mode before entering the auto-restart mode from the start-up mode.

The current inducing circuit 250 may include a secondary coil 252. The secondary coil 252 may carry a current induced by a changing magnetic field, such as the magnetic field induced by the primary coil 208. The solid line 240 indicates the magnetic coupling between the primary coil 208 and the secondary coil 252. The secondary coil 252 may, for example, include a wire such as a copper wire wrapped around a pot core. The secondary coil 252 may surround an aperture (not shown in FIG. 2) which receives the probe which surrounds the primary coil 208, with, for example, an air gap, such as an air gap of about 0.001 inches; the aperture is described further with reference to FIG. 6A.

The primary coil 208 and secondary coil 252 may form an isolation transformer with the coils of the primary coil 208 and secondary coil 252 wound around individual bobbins separated by the air gap. The transformer may be constructed in two sections corresponding to the primary coil 208 and the secondary coil 252, each wound on separate bobbins using one half of the pot core and separated by the magnetic air gap of 0.001 inches. The transformer may be designed to be discontinuous, so that energy may be transferred during the off time of the transistor 258.

The current inducing circuit 250 may include a delay switch 254 coupled to the secondary coil 252 and an output node 256 coupled to the delay switch 254. The delay switch 254 may delay the current carried by the secondary coil 252 from reaching the output node 256 to allow an output voltage of the output node 256 to reach a regulation voltage. The output node 256 may, for example, provide a voltage of approximately five volts direct current (DC) and 400 milliamperes.

The delay switch 254 may, for example, include a transistor 258, a first capacitor 260, and a first resistor 262. The transistor 258 may include a first end and a second end of a channel (such as a source and a drain) and a control node (such as a gate) which controls a resistance across the channel. The first end may be coupled to a first end of the secondary coil 252 and to a first end of the first capacitor 260. The second end may be coupled to the output node 256. The control node may be coupled to a second end of the first capacitor 260, all according to an example embodiment.

The first end of the first capacitor 260 may be coupled to the first end of the secondary coil 252 and to the first end of the channel of the transistor 258. The second end of the first capacitor 260 may be coupled to the control node of the transistor 258. A first end of the first resistor 262 may include a first end coupled to the second end of the first capacitor 260 and to the control node of the transistor 258, and a second end coupled to ground 264, all according to an example embodiment.

In an example embodiment, the transistor 258 may include a metal-oxide-semiconductor field-effect transistor (MOSFET). The transistor 258 may, for example, include a p-channel MOSFET. The channel may include a source-drain channel of the MOSFET, and the first end and second end may include a source and a drain, or vice versa. Also in this example, the control node may include a gate of the MOSFET.

The delay cause by the delay switch 254 may be a function of the RC time constant of the first capacitor 260 and the first resistor 262 and the saturation threshold of the transistor 258.

In an example in which the first capacitor 260 has a capacitance of approximately 0.15 microfarads and the first resistor 262 has a resistance of approximately one megaohm, the delay may be 150 milliseconds.

In an example embodiment, the current inducing circuit 250 may include a second capacitor 266. The second capacitor 266 may rectify and filter the output of the secondary coil 252 to provide a DC output at the output node 256.

The second capacitor 266 may have a capacitance of, for example, 22 microfarads and 63 volts. A first end of the second capacitor 266 may be coupled to the first end of the secondary coil 252, the first end of the first capacitor 260, and to the first end of the channel of the transistor 258. A second end of the second capacitor 266 may be coupled to the second end of the first resistor 262 and to ground 264, all according to an example embodiment.

Also in an example embodiment, the current inducing circuit 250 may include a first diode 268 and a third capacitor 270. The first diode 268 may, for example, include a Zener diode. The first diode 268 may prevent a voltage of the output node 256 from exceeding a breakdown voltage of the first diode 268, such as approximately 5.6 volts. The third capacitor 270 may reduce ripples in the voltage of the output node 256.

The third capacitor 270 may, for example, have a capacitance of 1000 microfarads and 6.3 volts. The first diode 268 may include a cathode end coupled to the second end of the channel of the transistor 258, to the output 256, and to a first end of the third capacitor 270. The first diode 268 may also include an anode end coupled to a second end of the third capacitor 270, to the ground 264, to the second end of the first resistor 262, and to the second end of the second capacitor 266. The first end of the third capacitor 270 may be coupled to the second end of the channel of the transistor 258, to the first end of the first diode 268, and to the output node 256. The second end of the third capacitor 270 may be coupled to ground 264, to the second end of the first diode 268, to the second end of the first resistor 262, and to the second end of the second capacitor 266, all according to an example embodiment.

In an example embodiment, the current inducing circuit 250 may include a second diode 272, such as a Schottky diode. The second diode 272 may rectify the output of the secondary coil 252 to provide a DC output at the output 256. The second diode 272 may include a cathode end coupled to a second end of the secondary coil, and an anode end coupled to the second end of the second capacitor 266, to the second end of the first resistor 262, to the anode end of the first diode 268, to the second end of the second capacitor 266, and to ground 264.

In an example embodiment, the current inducing circuit 250 may include a snubber circuit 274. The snubber circuit 274 may reduce transient voltages between the second end of the secondary coil 252 and the ground 264. The snubber circuit 274 may also attenuate conducted electromagnetic interference, such as in high frequency bands.

The snubber circuit 274 may, for example, include a fourth capacitor 276 and a second resistor 278 connected in series. The fourth capacitor 276 may have a capacitance of 0.001 microfarads and 100 volts, according to an example embodiment. A first end of the snubber circuit 274 or series may be coupled to the second end of the secondary coil 252 and to the cathode end of the second diode 272. A second end of the snubber circuit 274 or series may be coupled to the anode end of the second diode 272, to the second end of the second capacitor 266, to the second end of the first resistor 262, to the anode end of the first diode 268, to the second end of the third capacitor 270, and to ground 264, all according to an example embodiment.

Figure 6B:
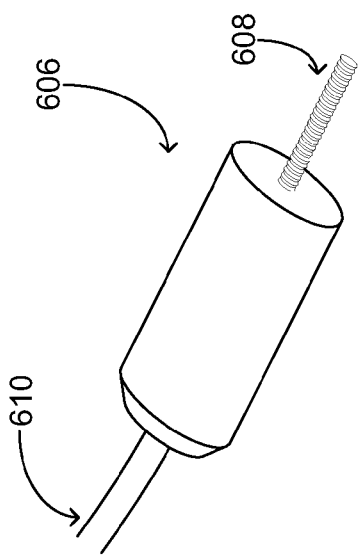
FIG. 6B is an illustration of a charging probe according to an example embodiment.
Figure 6D:
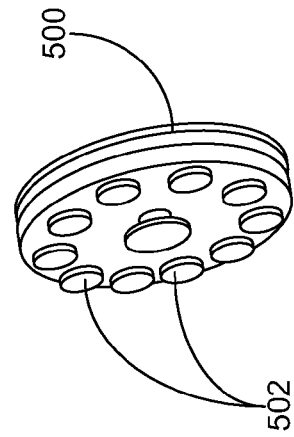
FIG. 6D is an illustration of a disk with a plurality of magnets according to an example embodiment.
Figure 6A:
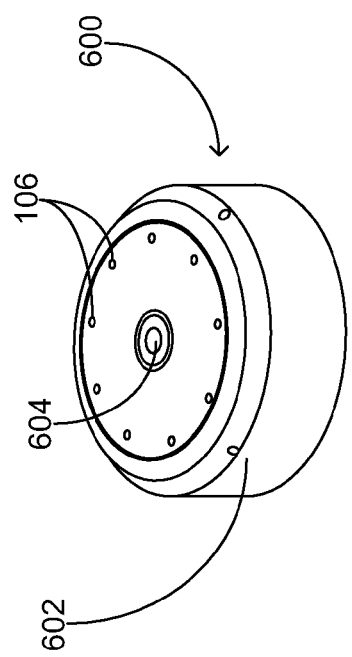
FIG. 6A is an illustration of a magnetic therapy device according to an example embodiment.

In an example embodiment, the current inducing circuit 250 may be included in a disk-shaped housing, such as the housing shown in FIG. 6A. The disk-shaped housing may enclose a disk with a plurality of magnets mounted onto the disk, such as the disk shown in FIG. 6D. The disk may rotate based on power received from the output node 256, according to an example embodiment.

Figure 3:
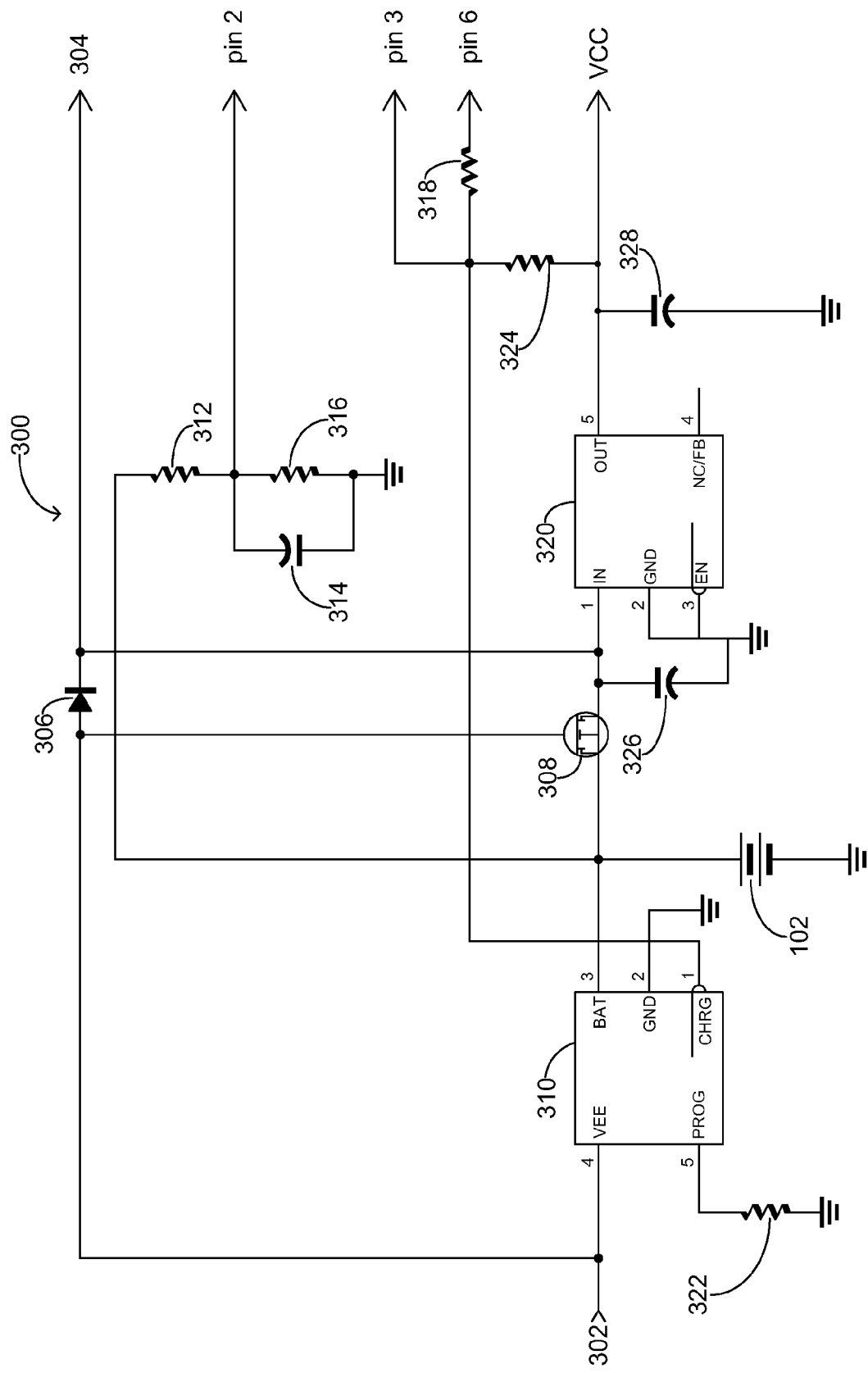
FIG. 3 is a circuit diagram showing a battery charging circuit according to an example embodiment.

FIG. 3 is a circuit diagram showing a battery charging circuit 300 according to an example embodiment. The battery charging circuit 300 may include, for example, a voltage source 302 coupled to a motor input 304 via a diode 306. The voltage source 302 may include, for example, the output node 256 shown in FIG. 2. The diode 306 may be coupled to the motor 104 (not shown in FIG. 3) and to the voltage source 302. The diode 306 may allow current to flow from the voltage source 302 to the motor 304. The motor input 304 may provide power to the motor 104. The motor 104 may spin a disk (shown in FIG. 6D) upon which a plurality of magnets are mounted, according to an example embodiment.

The battery charging circuit 300 may also include the rechargeable battery 102. The rechargeable battery 102 may, for example, include a lithium ion battery. The battery charging circuit 300 may recharge the rechargeable battery 102 with the voltage source 302, and may enable the rechargeable battery 102 to supply power to the motor 102, such as when a voltage of the voltage source 302 drops below a threshold voltage level, according to an example embodiment.

The battery charging circuit 300 may also include the rechargeable battery 102. The rechargeable battery 102 may, for example, include a lithium ion battery. The battery charging circuit 300 may recharge the rechargeable battery 102 with the voltage source 302, and may enable the rechargeable battery 102 to supply power to the motor 104, such as when a voltage of the voltage source 302 drops below a threshold voltage level, according to an example embodiment.

According to an example embodiment, the MOSFET 308 may include a p-channel MOSFET which allows current to flow from the rechargeable battery 102 through the MOSFET 308 to the motor input 304 only when a voltage level of the voltage source 302 drops below a threshold voltage value. In this example, the MOSFET 308 may allow the voltage source 302, but not the rechargeable battery 102, to supply power to the motor 104 via the motor input 304 when the voltage level of the voltage source 302 exceeds the threshold voltage value. However, when the voltage level of the voltage source 302 drops below the threshold voltage value, the rechargeable battery 102 may supply power to the motor 104 via the motor input 304. The diode 306, which may include a Schottky diode, may prevent current from flowing from the rechargeable battery 102 back to the voltage source 302.

In an example embodiment, the battery recharging circuit 300 may include a battery charger 310. The battery charger 310 may include a supply voltage pin (VEE) coupled to the voltage source 302, and a battery pin (BAT) coupled to the rechargeable battery 102. The battery charger 310 may, for example, include a single cell lithium-ion battery charger using a constant-current/constant voltage algorithm. The battery charger 310 may deliver 400 milliamperes of charge current with a final float voltage accuracy of ±1%. The battery charger 310 may include an internal p-channel MOSFET and thermal regulation circuitry.

According to an example embodiment, the battery charging circuit 300 may include a microprocessor 108 (not shown in FIG. 3). The microprocessor 108 may control the motor 104, and may include a voltage monitor pin (pin 2) which receives a signal from the rechargeable battery 102. The voltage monitor pin may be coupled to the rechargeable battery 102 via a first resistor 312, for example. The voltage monitor pin and first resistor 312 may be grounded via a first capacitor 314 and second resistor 316 connected in parallel, according to an example embodiment.

The first resistor 312 may, for example, have a resistance of about one megaohm. The second resistor 316 may, for example, have a resistance of about 100 kiloohms. The first capacitor 314 may, for example, have a capacitance of about 0.1 microfarads.

The microprocessor 108 may also include at least one charging monitor pin which receives a signal from a charge pin (CHRG) of the battery charger 310. The microprocessor 108 may, for example, include a pin 3 which is directly coupled to the charge pin of the battery charger 108, and a pin 6 which is coupled to the charge pin of the battery charger 108 via a third resistor 318. The third resistor 318 may, for example, have a resistance of about 2.49 kiloohms.

In an example embodiment, the battery charging circuit 300 may include a voltage regulator 320. The voltage regulator 320 may, for example, regulate the voltage of the rechargeable battery 102 and supply a regulated voltage VCC to the microprocessor 108. The regulated voltage VCC may, for example, be approximately 3.3 volts. The voltage regulator 320 may, for example, include a TPS77033 low-dropout voltage regulator with low dropout voltage, ultra-low power operation, and miniaturized packaging. A bypass capacitor 326, which may have a capacitance of about 0.1 microfarads, may improve transient response and noise rejection. An output capacitor 328, which may have a capacitance of about ten microfarads, may stabilize the internal control loop of the voltage regulator 320.

In an example embodiment, the battery charging circuit 300 may begin a charge cycle when a voltage at the voltage source 302 rises above an under voltage lock out (UVLO) threshold level with a fourth resistor 322 (which may, for example, have a resistance of about 2.49 kiloohms) coupled between a programming pin (PROG) of the battery charger 310 and ground, or when a battery is coupled to the charger output (CHRG) of the battery charger 310. If at battery pin (BAT) of the battery charger 310 falls below a threshold voltage level, such as approximately 2.9 volts, the battery charger may enter a trickle charge mode. In the trickle charge mode, the battery charger 310 may emit a current, such as approximately 40 milliamperes or ¹⁄₁₀ of a programmed charge current, from the charger output to bring the voltage of the rechargeable battery 102 to a safe level for full current charging. If the battery pin voltage rises above the threshold voltage level such as approximately 2.9 volts, the battery charger 310 may enter a constant-current mode, and may emit a current, such as 400 milliamperes or the programmed charge current, from the charger output to the rechargeable battery. If the battery pin reaches a final float voltage, such as 4.2 volts, the battery charger 310 may enter a constant-voltage mode and reduce the current emitted from the charger output. The charge cycle may end when the current drops below a threshold value, such as 40 milliamperes or ¹⁄₁₀ of the programmed value. At the end of the charge cycle, the battery charger 310 may stop providing any current through the battery pin.

The charge current may be programmed for the programmed value, such as 400 milliamperes, using the fourth resistor 322 between the programming pin to ground. The fourth resistor 322 may, for example, have a resistance of 2.49 kiloohms to set the programmed charge current at 400 milliamperes.

The battery charger 310 may detect the end of the charge cycle, such as by using an internal, filtered comparator to monitor the programming pin. The battery charger 310 may terminate charging when a voltage value of the programming pin falls below a threshold for a specified period of time, such as below 100 millivolts for one millisecond. In response to detecting the end of the charge cycle, the battery charger 310 may enter a standby mode and latch off the charge current. In the standby mode, the battery charger 310 may monitor the voltage level of the battery pin. If the voltage of the battery pin drops below a recharge threshold, such as approximately 4.05 volts, the battery charger 310 may begin another charge cycle and supply current to the rechargeable battery 102. The battery charger 310 may also begin another recharge cycle in response to the magnetic field being removed and reapplied to the secondary coil 252, such as when the charging probe (shown in FIG. 6B) is removed and reinserted.

In an example embodiment, the charger output of the battery charger 310 may have three states: a strong pull-down state, a weak pull-down state, and a high impedance state. In the strong pull-down state, a relatively large current, such as approximately twenty milliamperes, may flow out of the charger output. The strong pull-down state may indicate that the battery charger is in a charge cycle. Once the charge cycle has ended, the state of the charger output may be determined by undervoltage lockout conditions.

In the weak pull-down state, a relatively small current, such as approximately two milliamperes, may flow out of the charger output. The weak pull-down may indicate that the voltage source 302 meets the UVLO conditions and the battery charger 310 is ready to charge. The high impedance state, with no current flowing out of the charging output, may indicate that the battery charger 310 is in UVLO mode, because either the voltage source 302 is less than a threshold voltage, such as 100 millivolts, above the battery pin voltage, or insufficient voltage is applied to the voltage source 302.

In an example embodiment, the microprocessor 108 (not shown in FIG. 3) may distinguish between the strong pull-down, weak pull-down, and high impedance modes. The microprocessor 108 may, for example, detect the strong pull-down state indicating that the battery charger 310 is in a charge cycle by forcing a digital output pin 6 into a high impedance state and measuring a voltage at pin 3. An N-channel MOSFET (not shown), which may be included in the battery charger 310, may pull the charge pin low despite the voltage at the third resistor 318.

When the charge cycle has terminated and the charger output of the battery charger 310 is in the weak pull-down state, emitting the relatively small current, such as approximately two milliamperes, the voltage of the pin 3 may be pulled high by the third resistor 318. The microprocessor 108 may determine if there is a relatively small current indicating the weak pull-down state by, for example, forcing the digital output pin 6 into a low impedance state. The relatively high current may pull the pin 3 low through a fifth resistor 324, which may have a resistance of, for example, about one megaohm.

The microprocessor 108 may determine that the charger output is in the high impedance mode, indicating that the battery charger 310 is in UVLO mode, based on the pin 6 being pulled into a high impedance state and measuring the voltage on pin 3.

The microprocessor 108 may monitor the voltage of the rechargeable battery 102, such as via pin 2. Monitoring the voltage of the rechargeable battery 102 may allow the microprocessor 108 to determine the energy capacity of the rechargeable battery 102. The first resistor 312 and second resistor 316 may form a voltage divider network. The voltage divider network may scale the voltage to acceptable limits of the pin 2 of the microprocessor 108. The first capacitor 314 may act as a bypass capacitor. The microprocessor 108 may, for example, measure the voltage at pin 2 and multiply by the ratio of the first resistor 312 to the second resistor 316 to determine the voltage of the rechargeable battery 102.

In an example embodiment, a housing (shown in FIG. 6A) may enclose the voltage source 302, the diode 306, the rechargeable battery 102, and the motor 104. The housing may be disk-shaped, may include no electrical contacts on an outside surface of the housing, and/or may be waterproof.

Figure 4:
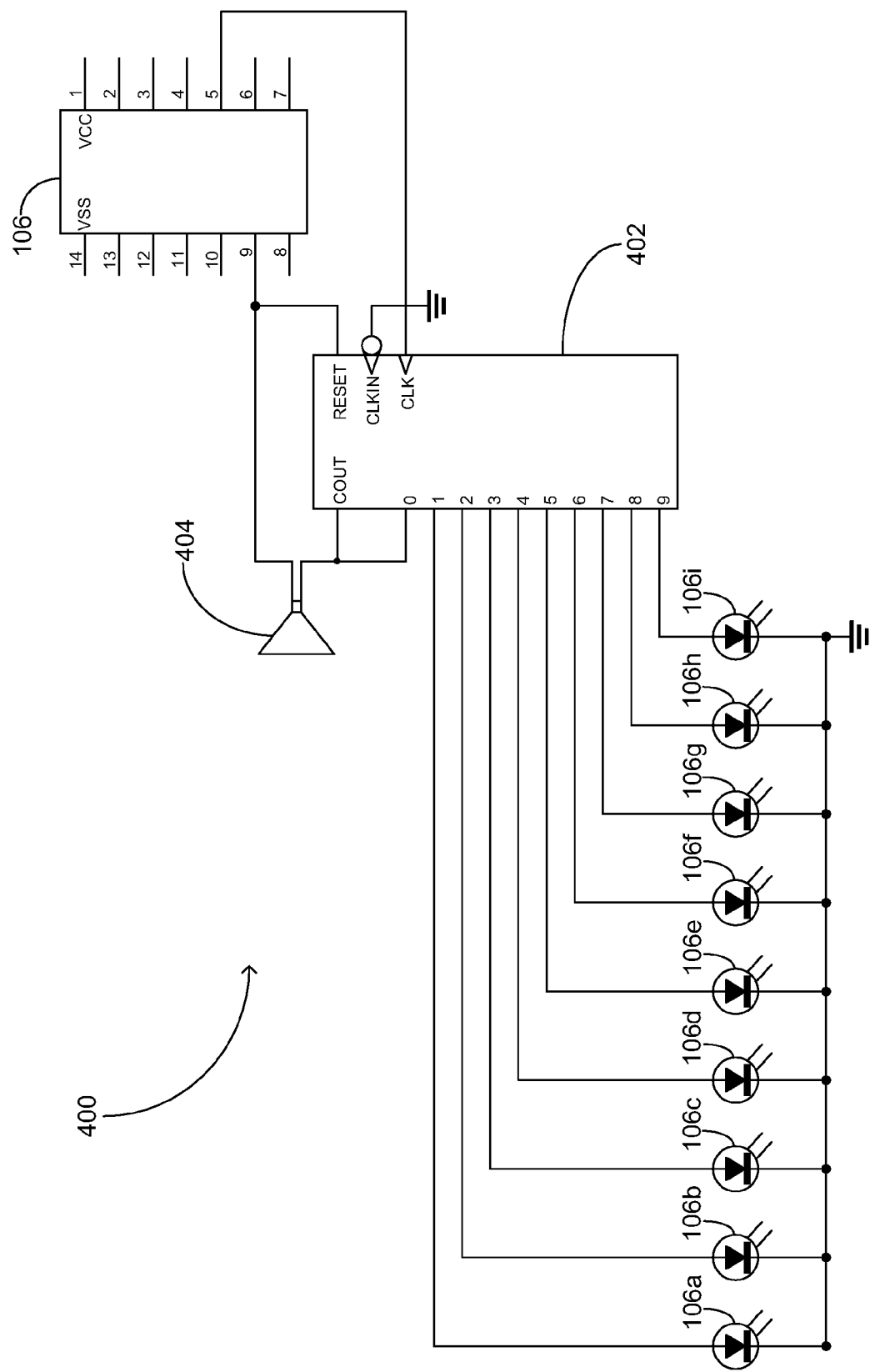
FIG. 4 is a circuit diagram showing a visual indicating circuit according to an example embodiment.

FIG. 4 is a circuit diagram showing the visual indicating circuit 400 according to an example embodiment. The visual indicating circuit 400 may include the microprocessor 108 and a plurality of visual indicators 106a, 106b, 106c, 106d, 106e, 106f, 106g, 106h, 106i. The plurality of visual indicators 106a, 106b, 106c, 106d, 106e, 106f, 106g, 106h, 106i may, for example, include a plurality of light-emitting diodes (LESs). While nine visual indicators 106a, 106b, 106c, 106d, 106e, 106f, 106g, 106h, 106i are shown in FIG. 4, the visual indicating circuit 400 may include any number of visual indicators.

The microprocessor 108 may monitor the voltage level of the rechargeable battery 102 (not shown in FIG. 4) and light a number of the plurality of visual indicators 106a, 106b, 106c, 106d, 106e, 106f, 106g, 106h, 106i. The number may, for example, be based on the monitored voltage level. For example, if the rechargeable battery 102 is fully charged, all of the plurality of visual indicators 106a, 106b, 106c, 106d, 106e, 106f, 106g, 106h, 106i may be turned on; if the rechargeable battery 102 is less than fully charged, then a proportionate number of the plurality of visual indicators 106a, 106b, 106c, 106d, 106e, 106f, 106g, 106h, 106i may be turned on. The microprocessor 108 may turn on the number of the plurality of visual indicators 106a, 106b, 106c, 106d, 106e, 106f, 106g, 106h, 106i by turning the number of the plurality of visual indicators 106a, 106b, 106c, 106d, 106e, 106f, 106g, 106h, 106i on and off at a frequency that is imperceptible to a human eye, according to an example embodiment.

While not shown in FIG. 4, the visual indicating circuit 400 may also include the motor 104 which spins the disk upon which is mounted the plurality of magnets. As shown in FIG. 6D, the plurality of magnets may be mounted onto the disk in a circular pattern with alternating polarities. The microprocessor 108 may, for example, cause the motor 104 to spin the disk for a predetermined time duration. While the motor 104 is spinning the disk, the microprocessor 108 may light all of the plurality of visual indicators 106a, 106b, 106c, 106d, 106e, 106f, 106g, 106h, 106i in a rotational sequence, according to an example embodiment. The microprocessor may light all of the plurality of visual indicators 106a, 106b, 106c, 106d, 106e, 106f, 106g, 106h, 106i in the rotational sequence by, for example, periodically providing clock pulses to the counter 402. A frequency of the lighting the plurality of visual indicators 106a, 106b, 106c, 106d, 106e, 106f, 106g, 106h, 106i in the rotational sequence may increase during an end portion of the predetermined time duration. The increase in the frequency may alert a user that the therapy cycle is almost over.

While also not shown in FIG. 4, the visual indicating circuit 400 may also include the rechargeable battery 102 which supplies power to the motor 104. The rechargeable battery 102 may also supply power to the microprocessor 108, such as via the voltage regulator 320 (not shown in FIG. 4). According to an example embodiment, the microprocessor 108 may cause the motor 104 to spin the disk upon determining that an outside power source (such as the magnetic field induced by the charging probe circuit 200) has been removed from the visual indicating circuit 400 and/or the rechargeable battery 202, and/or upon determining that the voltage level of the rechargeable battery 102 exceeds a threshold voltage level.

The microprocessor 108 may, for example, light the plurality of visual indicators 106a, 106b, 106c, 106d, 106e, 106f, 106g, 106h, 106i via a counter 402. The counter 402 may, for example, include a CD74HC 4017 decade counter clocked by the microprocessor 108. The counter 402 may include a high-speed silicon gate complimentary metal-oxide semiconductor (CMOS) five-stage Johnson counter with ten decoded outputs. The outputs may normally remain low, and sequentially transition from low to high at the low to high transitions of the clock input (CLK).

The microprocessor 108 may light the plurality of visual indicators 106a, 106b, 106c, 106d, 106e, 106f, 106g, 106h, 106i via the counter 402 by, for example, periodically providing a number of clock pulses and a reset pulse to the counter 402. For example, the microprocessor 108 may sequentially provide a number of clock pulses to the counter 402 equal to the number of the plurality of visual indicators 106a, 106b, 106c, 106d, 106e, 106f, 106g, 106h, 106i which are to light or turn on, and then provide the reset pulse to the counter 402. After providing the reset pulse to the counter 402, the microprocessor 108 may provide the number of clock pulses to the counter 402 and then the reset pulse, and so on. The microprocessor 108 may provide the clock pulses by providing inputs to a clock pin (CLK) of the counter 402, and may provide the reset pulses by providing inputs to a reset pin (RESET) of the counter 402, according to an example embodiment.

According to an example embodiment, the visual indicating circuit 400 may include an audible output element 404. The audible output element 404 may, for example, include a piezoelectric horn capable of producing high frequency beeps, and may be driven by the counter 402. The microprocessor 108 may, for example, cause the audible output element 404 to periodically emit an audible output, such as a beep, when the motor 104 is spinning.

The visual indicating circuit 400 may be included in a housing (shown in FIG. 6A). The housing may enclose the motor 104, the disk, the rechargeable battery 102, and the microprocessor 108. The plurality of visual indicators 106a, 106b, 106c, 106d, 106e, 106f, 106g, 106h, 106i may be mounted in the housing. The housing may be disk-shaped, include no electrical contacts on an outside surface of the housing, and/or may be waterproof.

Figure 5:
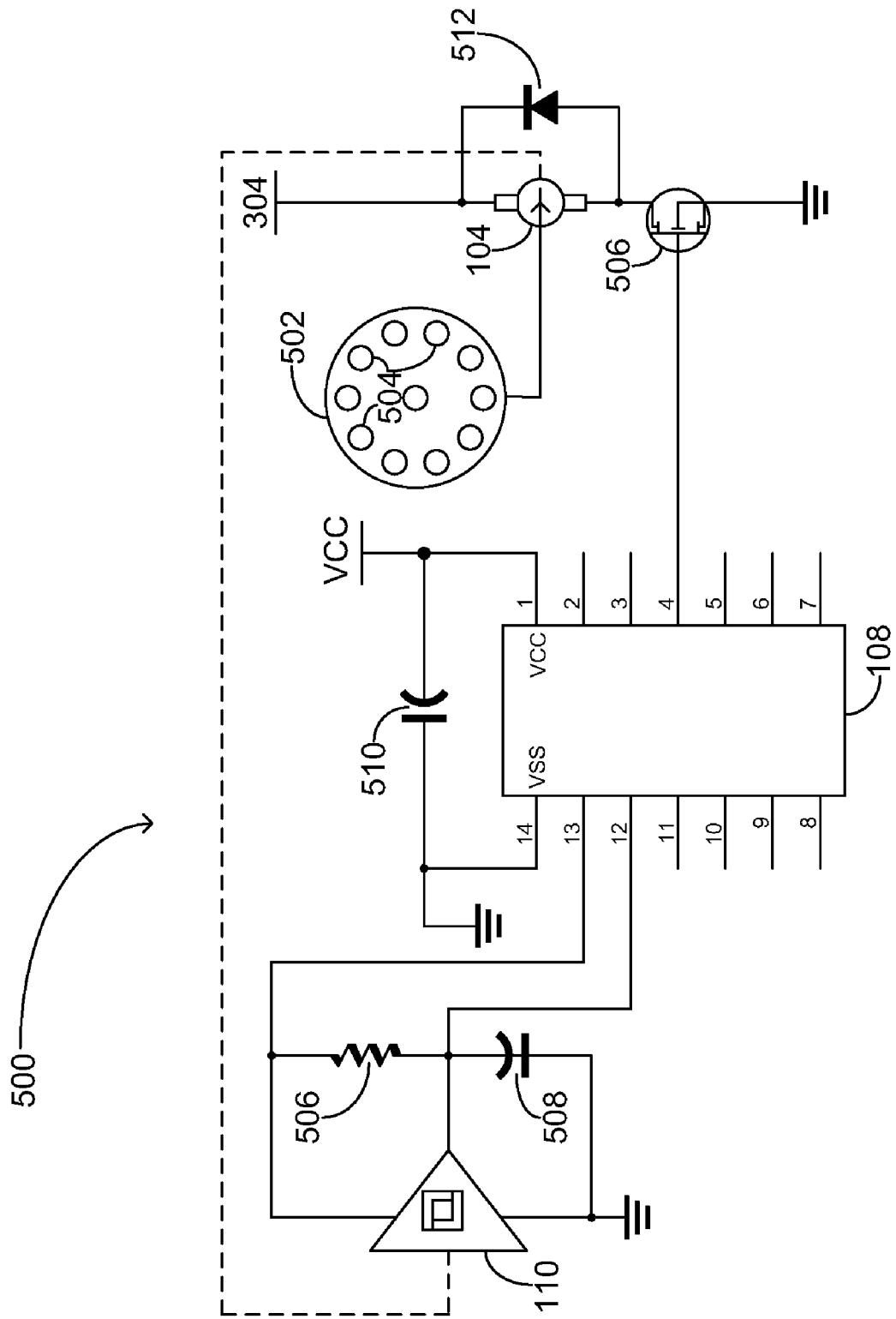
FIG. 5 is a circuit diagram showing a tachometer circuit according to an example embodiment.

FIG. 5 is a circuit diagram showing the tachometer circuit 500 according to an example embodiment. The tachometer circuit 500 may include, for example, a power source or motor input 304 which supplies power to the motor 104. The power source may, for example, include the rechargeable battery 102. The tachometer circuit 500 may also include the motor 104. The motor 104, which may include a direct current (DC) motor, may control a disk 502 upon which a plurality of magnets 504 may be mounted. The magnets 504 may, for example, be mounted onto the disk 502 in a circular manner with alternating polarities.

The tachometer circuit 500 may also include the tachometer 110. The tachometer 110 may, for example, include a Melexis US4881, which may include a bipolar Hall-effect switch designed with mixed signal CMOS technology. The tachometer 110 may integrate a voltage regulator, Hall sensor with a dynamic offset cancellation system, a Schmitt trigger, and an open-drain output driver. The power to operate the tachometer 110, which may have a voltage of 3.3 volts in an example embodiment, may be provided by the microprocessor 108, which in turn may be powered by the regulated voltage VCC.

The tachometer 110 may monitor a magnetic field generated by the plurality of magnets 504 and provide a signal to the microprocessor 108 based on the monitored magnetic field. The magnetic coupling of the tachometer 110 to the magnetic field generated by the magnets 504 spinning around the motor 104 is shown by the dashed line in FIG. 5. The tachometer 110 may, for example, monitor a frequency of magnetic flux generated by the plurality of magnets 504 and provide the signal to the microprocessor 108 based on the frequency of magnetic flux. The signal may, for example, include a pulse for each change of magnetic flux, or pulses with a frequency proportional to the speed of rotation of the disk 502.

A resistor 506, which may have a resistance of ten kiloohms in an example embodiment, may cause the signal output by the tachometer 110 to have a voltage value between zero and the regulated voltage VCC, and may be about 3.3 volts in an example embodiment. A filter capacitor 508, which may have a capacitance of 0.001 microfarads in an example embodiment, may filter out noise and stabilize the detected magnetic frequency.

The magnetic frequency generated by the magnets 504 may be a function of the number of poles and the rotation speed of the disk 502. In an example in which the disk 502 includes ten poles (ten magnets 504 with alternating polarities N-S-N-S-N-S-N-S-N-S), one complete rotation by the disk 502 may generate five sinusoidal magnetic cycles. The motor 104 may generate a prescribed frequency of, for example, 100 magnetic cycles per second (CPS) by rotating the disk 502 twenty rotations per second (20 rotations per second×5 sinusoidal magnetic cycles per rotation=100 cycles per second).

The tachometer circuit 500 may also include a microprocessor, which may be the same microprocessor 108 included in the visual indicating circuit 400. A capacitor 510, which may have a capacitance of 0.15 microfarads in an example embodiment, may reduce high frequency noise on the regulated voltage VCC. The microprocessor 108 may control the motor 104 based on the signal received from the tachometer 110. The microprocessor 108 may, for example, control the motor 104 based on the signal by comparing the signal to a reference signal. In an example embodiment, the microprocessor 108 may cause the motor 104 to increase or decrease the speed of rotation of the disk 502 and magnets 504 to maintain a desired strength of the magnetic field.

The microprocessor 108 may control the motor 104 by controlling a current flowing through the motor 104. The motor 104 may, for example, include a precision DC motor with gold brushes. For example, if the microprocessor 108 determines, based on the signal received from the tachometer 110, that the frequency of magnetic flux is too low, the microprocessor 108 may increase the speed of rotation of the disk 502 by allowing current to flow through the motor 104. Or, if the microprocessor 108 determines that the frequency of magnetic flux is too high, the microprocessor may decrease the speed of rotation of the disk 502 by not allowing current to flow through the motor 104. The microprocessor 108 may control the motor 104 by applying an input to a transistor 506 which is connected in series with the motor 104. The input may, for example, take the form of pulse width modulation (PWM). Applying the input to the transistor 506 may vary a resistance of the transistor 506 and thereby vary the power available to the motor 104 to spin the disk 502. The transistor 506 may, for example, include a metal-oxide-semiconductor field-effect transistor (MOSFET); in this example, the microprocessor 108 may control the motor 104 by controlling a voltage applied to a gate of the MOSFET. A diode 512 may allow any reverse-biased voltage to dissipate without causing the motor 104 to reverse direction.

The tachometer circuit 500 may, for example, be included in a housing (shown in FIG. 6A). The housing may, for example, enclose the power source or motor input 304, the motor 104, the disk 502, the tachometer 110, and the microprocessor 108. The housing may be disk-shaped, have no electrical contacts on an outside surface of the house, and/or may be waterproof.

FIG. 6A is an illustration of a magnetic therapy device 600 according to an example embodiment. The magnetic therapy device 600 may, for example, include a housing 602. The housing 602 may be disk-shaped, such as approximately the size of a hockey puck. The housing 602 may, for example, have a five inch diameter and be two inches thick. The housing 602 may include a Velcro strip (not shown), enabling a user to secure the magnetic therapy device to his or her body. The housing 602 may have not electrical contacts on an outside surface of the housing 602, according to an example embodiment. The housing 602 may be waterproof. The housing may include an aperture 604.

The magnetic therapy device 600 may include the current inducing circuit 250 (not shown in FIG. 6A). The current inducing circuit 250 may be mounted onto an inside surface (not shown) of the housing 602.

The current inducing circuit 250 may convert a magnetic field into a direct current (DC) voltage. In an example embodiment, the current inducing circuit 250 may include the secondary coil 252. The secondary coil 252 may induce a current from the magnetic field. The secondary coil 252 may surround the aperture 604. The current inducing circuit 250 may also include the delay switch 254 and the output node 256. The delay switch 254 may be coupled to the secondary coil 252, and the output node 256 may be coupled to the delay switch 254 and to the battery charging circuit 300.

The magnetic therapy device 600 may also include the battery charging circuit 300 (not shown in FIG. 6A). The battery charging circuit 300 may be enclosed by the housing 602. The battery charging circuit 300 may charge the rechargeable battery 102 based on the DC voltage. The battery charging circuit 300 may also, based on the rechargeable battery 102, supply power to the motor 104 and to the microprocessor 108.

The magnetic therapy device 600 may also include the microprocessor 108 (not shown in FIG. 6A). The microprocessor 108 may be enclosed by the housing 102. The microprocessor 108 may control the plurality of visual indicators 106*a*, 106*b*, 106*c*, 106*d*, 106*e*, 106*f*, 106*g*, 106*h*, 106*i*. The microprocessor 108 may also control the motor 104. The microprocessor 108 may, for example, be programmed so that each therapy cycle of the magnetic therapy device 600, in which the motor 104 spins the disk 502 with the plurality of magnets 504, lasts approximately twenty minutes. The rechargeable battery 102 may, when fully charged, have enough energy to power twenty such therapy cycles, according to an example embodiment.

The magnetic therapy device 600 may also include the plurality of visual indicators 106*a*, 106*b*, 106*c*, 106*d*, 106*e*, 106*f*, 106*g*, 106*h*, 106*i*. The plurality of visual indicators 106*a*, 106*b*, 106*c*, 106*d*, 106*e*, 106*f*, 106*g*, 106*h*, 106*i* may be mounted onto the housing 602, and may emit light outside the magnetic therapy device 600. While nine visual indicators 106*a*, 106*b*, 106*c*, 106*d*, 106*e*, 106*f*, 106*g*, 106*h*, 106*i* are shown, the magnetic therapy device 600 may include any number of visual indicators 106*a*, 106*b*, 106*c*, 106*d*, 106*e*, 106*f*, 106*g*, 106*h*, 106*i*. The visual indicators 106*a*, 106*b*, 106*c*, 106*d*, 106*e*, 106*f*, 106*g*, 106*h*, 106*i* may indicate both the charge state of the rechargeable battery 102 and the progress of a therapy cycle.

The magnetic therapy device 600 may also include the motor 104 (not shown in FIG. 6A). The motor 104 may generate a magnetic field by spinning the disk 502 upon which the plurality of magnets 504 are mounted.

FIG. 6B is an illustration of a charging probe 606 according to an example embodiment. The charging probe 606 may include the charging probe circuit 200 (not shown in FIG. 6B). The primary coil 208 may, for example, be included in a probe 608 which fits into the aperture 604 of the housing. The AC input 202 may, for example, be included in an electrical power cord 610 which may plug into an electrical outlet to receive AC power. The electrical power cord 610 may, for example, receive power from sources between about 85 and 275 volts AC and/or 47 to 63 Herz, allowing the charging probe 606 to charge the magnetic therapy device 600 from many electrical outlets.

Figure 6C:
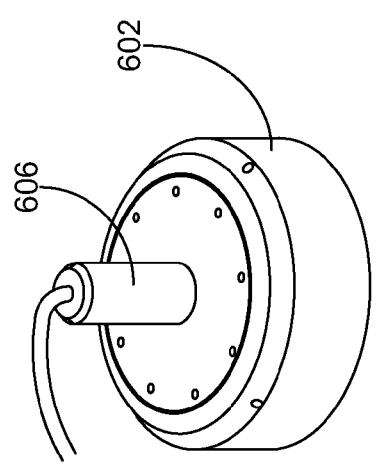
FIG. 6C is an illustration of the magnetic therapy device with the charging probe inserted according to an example embodiment.

FIG. 6C is an illustration of the magnetic therapy device 600 with the charging probe 606 inserted according to an example embodiment. The charging probe 606 may, in the inserted position, supply power to the magnetic therapy device 600 with no electrical contacts.

FIG. 6D is an illustration of the disk 502 with the plurality of magnets 504 according to an example embodiment. The magnets 504 may be mounted onto the disk 502 in a circular pattern with alternating polarities.

The magnetic therapy device 600 may, in an example embodiment, be self-contained, needing no outside components or inputs except the charging probe 606. The magnetic therapy device 600 may be waterproof and/or water submersible, enabling a person to use the magnetic therapy device 600 in a bathtub, for example. The magnetic therapy device may also be cleaned with soap and water, for example.

The magnetic therapy device 600 may also have no electrical contacts and rely completely on the rechargeable battery 102, which may be magnetically coupled to the charging probe 606, for power. The transfer of energy from the charging probe 606 to the magnetic therapy device 606 by the magnetic field may make the magnetic therapy device safe from electrical shock hazards. The magnetic therapy device 600 may have no switches, push buttons, or other such controls other than the charging probe 606.

Processors suitable for the execution of a computer program include, by way of example, both general and special purpose microprocessors, and any one or more processors of any kind of digital computer. Generally, a processor will receive instructions and data from a read-only memory or a random access memory or both. Elements of a computer may include at least one processor for executing instructions and one or more memory devices for storing instructions and data. Generally, a computer also may include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory may be supplemented by, or incorporated in special purpose logic circuitry.

Implementations may be implemented in a computing system that includes a back-end component, e.g., as a data server, or that includes a middleware component, e.g., an application server, or that includes a front-end component, e.g., a client computer having a graphical user interface or a Web browser through which a user can interact with an implementation, or any combination of such back-end, middleware, or front-end components. Components may be interconnected by any form or medium of digital data communication, e.g., a communication network. Examples of communication networks include a local area network (LAN) and a wide area network (WAN), e.g., the Internet.

While certain features of the described implementations have been illustrated as described herein, many modifications, substitutions, changes and equivalents will now occur to those skilled in the art. It is, therefore, to be understood that the appended claims are intended to cover all such modifications and changes as fall within the true spirit of the embodiments of the invention.

What is claimed is:

1. A magnetic therapy device comprising:
a power source configured to supply power to a motor;
the motor, the motor being configured to control a disk upon which is mounted a plurality of magnets;
a tachometer, the tachometer being configured to monitor a frequency of magnetic flux generated by the plurality of magnets and provide a signal to a microprocessor based on the frequency of magnetic flux; and
the microprocessor, the microprocessor being configured to control the motor based on the signal received from the tachometer.

2. The magnetic therapy device of claim 1, wherein the power source includes a rechargeable battery.

3. The magnetic therapy device of claim 1, wherein the motor includes a direct current (DC) motor.

4. The magnetic therapy device of claim 1, wherein the plurality of magnets are mounted onto the disk in a circular manner with alternating polarities.

5. The magnetic therapy device of claim 1, wherein the tachometer is configured to monitor the frequency of magnetic flux generated by the plurality of magnets and provide the signal to the microprocessor based on the frequency of magnetic flux, the signal including a pulse for each change of magnetic flux.

6. The magnetic therapy device of claim 1, wherein the tachometer is configured to monitor the magnetic flux generated by the plurality of magnets and provide the signal to the microprocessor, the signal including pulses with a frequency proportional to a speed of rotation of the disk.

7. The magnetic therapy device of claim 1, wherein the microprocessor is configured to control the motor based on the signal by comparing the signal to a reference signal.

8. The magnetic therapy device of claim 1, wherein the microprocessor is configured to control the motor by controlling a current flowing through the motor.

9. The magnetic therapy device of claim 1, wherein the microprocessor is configured to control the motor by applying an input to a transistor which is connected in series with the motor.

10. The magnetic therapy device of claim 1, wherein the microprocessor is configured to control the motor by controlling a voltage applied to a gate of a metal-oxide-semiconductor field-effect transistor (MOSFET), the MOSFET being connected in series with the motor.

11. The apparatus of claim 1, the apparatus further including a housing which encloses the power source, the motor, the disk, the tachometer, and the microprocessor.

12. The apparatus of claim 11, wherein the housing is disk-shaped.

13. The apparatus of claim 11, wherein the housing includes no electrical contacts on an outside surface of the housing.

14. The apparatus of claim 11, wherein the housing is waterproof.

15. A magnetic therapy device comprising:
a power source configured to supply power to a motor;
the motor, the motor being configured to control a disk upon which is mounted a plurality of magnets;
a tachometer, the tachometer being configured to monitor a magnetic field generated by the plurality of magnets and provide a signal to a microprocessor based on the monitored magnetic field; and
the microprocessor, the microprocessor being configured to control the motor based on the signal received from the tachometer by applying an input to a transistor which is connected in series with the motor.

16. The magnetic therapy device of claim 15, wherein the power source includes a rechargeable battery.

17. The magnetic therapy device of claim 15, wherein the motor includes a direct current (DC) motor.

18. The apparatus of claim 15, the apparatus further including a housing which encloses the power source, the motor, the disk, the tachometer, and the microprocessor.

19. The apparatus of claim 18, wherein the housing is disk-shaped.

20. A magnetic therapy device comprising:
a power source configured to supply power to a motor;
the motor, the motor being configured to control a disk upon which is mounted a plurality of magnets;
a tachometer, the tachometer being configured to monitor a magnetic field generated by the plurality of magnets and provide a signal to a microprocessor based on the monitored magnetic field; and
the microprocessor, the microprocessor being configured to control the motor based on the signal received from the tachometer by controlling a voltage applied to a gate of a metal-oxide-semiconductor field-effect transistor (MOSFET), the MOSFET being connected in series with the motor.

* * * * *

UNITED STATES PATENT AND TRADEMARK OFFICE
CERTIFICATE OF CORRECTION

| | | |
|---|---|---|
| PATENT NO. | : 8,257,242 B2 | Page 1 of 1 |
| APPLICATION NO. | : 11/875477 | |
| DATED | : September 4, 2012 | |
| INVENTOR(S) | : George Sotiriou | |

It is certified that error appears in the above-identified patent and that said Letters Patent is hereby corrected as shown below:

In column 16, line 12, in claim 11, delete "apparatus" and insert -- magnetic therapy device --, therefor.

In column 16, line 15, in claim 12, delete "apparatus" and insert -- magnetic therapy device --, therefor.

In column 16, line 17, in claim 13, delete "apparatus" and insert -- magnetic therapy device --, therefor.

In column 16, line 20, in claim 14, delete "apparatus" and insert -- magnetic therapy device --, therefor.

In column 16, line 38, in claim 18, delete "apparatus" and insert -- magnetic therapy device --, therefor.

In column 16, line 41, in claim 19, delete "apparatus" and insert -- magnetic therapy device --, therefor.

Signed and Sealed this
First Day of January, 2013

David J. Kappos
*Director of the United States Patent and Trademark Office*